US012128188B2

(12) United States Patent
Cheng et al.

(10) Patent No.: US 12,128,188 B2
(45) Date of Patent: Oct. 29, 2024

(54) DYNAMIC PRESSURE RESPONSE SYSTEM AND METHOD FOR MEASURING RESIDUAL FLUID

(71) Applicant: C. R. Bard, Inc., Franklin Lakes, NJ (US)

(72) Inventors: Jason Jishen Cheng, Avondale Estates, GA (US); Christopher K. Brooks, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/556,942

(22) Filed: Dec. 20, 2021

(65) Prior Publication Data

US 2022/0193366 A1 Jun. 23, 2022

Related U.S. Application Data

(60) Provisional application No. 63/128,597, filed on Dec. 21, 2020.

(51) Int. Cl.
*A61M 25/00* (2006.01)

(52) U.S. Cl.
CPC . *A61M 25/0017* (2013.01); *A61M 2205/3331* (2013.01); *A61M 2205/3379* (2013.01); *A61M 2205/50* (2013.01); *A61M 2210/1085* (2013.01)

(58) Field of Classification Search
CPC ........ A61M 25/001; A61M 2205/3331; A61M 2205/3379; A61M 2205/50; A61M 2210/1085
See application file for complete search history.

(56) References Cited

U.S. PATENT DOCUMENTS

| 3,114,916 A | 12/1963 | Hadley |
| 3,583,401 A | 6/1971 | Vailiancourt et al. |

(Continued)

FOREIGN PATENT DOCUMENTS

| EP | 1872752 A1 | 1/2008 |
| EP | 2417955 A2 | 2/2012 |

(Continued)

OTHER PUBLICATIONS

PCT/US2020/066707 filed Dec. 22, 2020 International Search Report and Written Opinion dated Apr. 15, 2021.

(Continued)

*Primary Examiner* — Leslie A Lopez
*Assistant Examiner* — Katherine-Ph Minh Pham
(74) *Attorney, Agent, or Firm* — Rutan & Tucker LLP

(57) ABSTRACT

Embodiments disclosed herein are directed to a dynamic pressure response drainage system including control logic configured to enable measuring of residual fluid disposed within the drainage lumen. The residual fluid volume is measured by detecting the magnitude of the dynamic pressure response in the system containing the residual fluid when a sudden displacement (e.g. increase or decrease) of air volume occurs inside the system. The pressure burst magnitude is related to the pressure needed to move the mass of fluid, thus the fluid volume can be calculated from measurements of the burst pressure. The magnitude of the measured air pressure exhibits a dynamic pressure response corresponding to the mass of fluid in the tube. Either positive or negative pressure bursts can be used to produce and measure the corresponding positive or negative dynamic response spike pressure.

22 Claims, 3 Drawing Sheets

(56) References Cited

U.S. PATENT DOCUMENTS

| | | | |
|---|---|---|---|
| 3,598,124 A | 8/1971 | Andersen et al. | |
| 3,661,143 A | 5/1972 | Henkin | |
| 3,861,394 A | 1/1975 | Villari | |
| 3,901,235 A | 8/1975 | Patel et al. | |
| 3,955,574 A | 5/1976 | Rubinstein | |
| 4,084,593 A | 4/1978 | Jarund | |
| 4,265,243 A | 5/1981 | Taylor | |
| 4,305,403 A | 12/1981 | Punn | |
| 4,315,506 A | 2/1982 | Kayser et al. | |
| 4,360,933 A | 11/1982 | Kimura et al. | |
| 4,465,485 A | 8/1984 | Kashmer et al. | |
| 4,531,939 A | 7/1985 | Izumi | |
| 4,631,061 A | 12/1986 | Martin | |
| 4,654,029 A | 3/1987 | D'Antonio | |
| 4,747,166 A | 5/1988 | Kuntz | |
| 4,819,684 A | 4/1989 | Zaugg et al. | |
| 4,872,579 A | 10/1989 | Palmer | |
| 4,990,137 A | 2/1991 | Graham | |
| 5,002,528 A | 3/1991 | Palestrant | |
| 5,071,411 A | 12/1991 | Hillstead | |
| 5,186,431 A | 2/1993 | Tamari | |
| 5,318,550 A | 6/1994 | Cermak et al. | |
| 5,405,319 A | 4/1995 | Abell et al. | |
| 5,738,656 A | 4/1998 | Wagner et al. | |
| 5,813,842 A | 9/1998 | Tamari | |
| 5,894,608 A | 4/1999 | Birbara | |
| 6,007,521 A | 12/1999 | Bidwell et al. | |
| 6,106,506 A | 8/2000 | Abell et al. | |
| 6,183,454 B1 | 2/2001 | Evine et al. | |
| 8,266,741 B2 | 9/2012 | Penninger et al. | |
| 8,337,475 B2 | 12/2012 | Christensen et al. | |
| 8,475,419 B2* | 7/2013 | Eckermann | A61M 1/70 604/311 |
| 8,512,301 B2 | 8/2013 | Ma | |
| 10,391,275 B2* | 8/2019 | Burnett | A61M 25/0017 |
| 10,426,919 B2* | 10/2019 | Erbey, II | A61M 25/10 |
| 10,506,965 B2* | 12/2019 | Cooper | A61B 5/208 |
| 10,737,057 B1 | 8/2020 | Mikhail et al. | |
| 10,772,998 B2* | 9/2020 | Luxon | A61M 1/742 |
| 2002/0000253 A1 | 1/2002 | Fillmore et al. | |
| 2002/0161317 A1 | 10/2002 | Risk et al. | |
| 2003/0078638 A1 | 4/2003 | Voorhees et al. | |
| 2004/0176746 A1 | 9/2004 | Forral | |
| 2004/0230181 A1 | 11/2004 | Cawood | |
| 2004/0236292 A1 | 11/2004 | Tazoe et al. | |
| 2004/0254547 A1 | 12/2004 | Okabe et al. | |
| 2005/0209585 A1 | 9/2005 | Nord et al. | |
| 2005/0245898 A1 | 11/2005 | Wright et al. | |
| 2005/0261619 A1 | 11/2005 | Gay | |
| 2006/0015190 A1 | 1/2006 | Robertson | |
| 2006/0079854 A1 | 4/2006 | Kay et al. | |
| 2006/0155260 A1 | 7/2006 | Blott et al. | |
| 2006/0235353 A1 | 10/2006 | Gelfand et al. | |
| 2006/0270971 A1 | 11/2006 | Gelfand et al. | |
| 2006/0271019 A1 | 11/2006 | Stoller et al. | |
| 2007/0078444 A1 | 4/2007 | Larsson | |
| 2007/0142729 A1 | 6/2007 | Pfeiffer et al. | |
| 2007/0272311 A1 | 11/2007 | Trocki et al. | |
| 2008/0156092 A1 | 7/2008 | Boiarski | |
| 2009/0157016 A1 | 6/2009 | Adahan | |
| 2009/0157040 A1* | 6/2009 | Jacobson | A61M 5/16804 702/45 |
| 2009/0326483 A1 | 12/2009 | Green | |
| 2010/0106116 A1 | 4/2010 | Simmons et al. | |
| 2010/0130949 A1 | 5/2010 | Garcia | |
| 2011/0060300 A1 | 3/2011 | Weig et al. | |
| 2012/0036638 A1 | 2/2012 | Penninger et al. | |
| 2012/0323144 A1 | 12/2012 | Coston et al. | |
| 2013/0218106 A1 | 8/2013 | Coston et al. | |
| 2014/0200558 A1 | 7/2014 | McDaniel | |
| 2015/0126975 A1 | 5/2015 | Wuthier | |
| 2015/0290448 A1 | 10/2015 | Pavlik | |
| 2016/0135982 A1 | 5/2016 | Garcia | |
| 2016/0183819 A1 | 6/2016 | Burnett et al. | |
| 2016/0310711 A1 | 10/2016 | Luxon et al. | |
| 2017/0072125 A1 | 3/2017 | Wallenås et al. | |
| 2017/0136209 A1 | 5/2017 | Burnett et al. | |
| 2017/0143566 A1 | 5/2017 | Elku et al. | |
| 2017/0241978 A1 | 8/2017 | Duval | |
| 2017/0312114 A1 | 11/2017 | Glithero | |
| 2018/0015251 A1 | 1/2018 | Lampotang et al. | |
| 2018/0071441 A1 | 3/2018 | Croteau et al. | |
| 2018/0104391 A1 | 4/2018 | Luxon et al. | |
| 2018/0110456 A1 | 4/2018 | Cooper et al. | |
| 2018/0125697 A1 | 5/2018 | Ferrera | |
| 2018/0177458 A1 | 6/2018 | Burnett et al. | |
| 2018/0235523 A1* | 8/2018 | Sauder | A61M 5/142 |
| 2018/0245699 A1 | 8/2018 | Lee | |
| 2018/0360424 A1 | 12/2018 | Yurek et al. | |
| 2019/0009021 A1 | 1/2019 | Nelson et al. | |
| 2019/0009023 A1* | 1/2019 | Diperna | A61M 5/16877 |
| 2019/0038451 A1 | 2/2019 | Harvie | |
| 2019/0046102 A1 | 2/2019 | Kushnir et al. | |
| 2019/0126006 A1 | 5/2019 | Rehm et al. | |
| 2019/0143094 A1 | 5/2019 | DeMeritt | |
| 2019/0151610 A1 | 5/2019 | Fletter | |
| 2019/0343445 A1 | 11/2019 | Burnett et al. | |
| 2020/0000979 A1 | 1/2020 | Myers | |
| 2020/0061281 A1 | 2/2020 | Desouza et al. | |
| 2020/0315837 A1 | 10/2020 | Radl et al. | |
| 2021/0077007 A1 | 3/2021 | Jouret et al. | |
| 2022/0152345 A1 | 5/2022 | Simiele et al. | |
| 2022/0160949 A1 | 5/2022 | Simiele et al. | |
| 2022/0176031 A1 | 6/2022 | Cheng et al. | |
| 2022/0218890 A1 | 7/2022 | Chavan | |
| 2022/0218973 A1 | 7/2022 | Chavan et al. | |
| 2022/0218974 A1 | 7/2022 | Chavan et al. | |
| 2022/0273213 A1 | 9/2022 | Sokolov et al. | |
| 2022/0305189 A1 | 9/2022 | Chavan et al. | |
| 2022/0330867 A1 | 10/2022 | Conley et al. | |
| 2022/0362080 A1 | 11/2022 | McCorquodale et al. | |
| 2022/0409421 A1 | 12/2022 | Hughett et al. | |
| 2023/0013353 A1 | 1/2023 | Chavan et al. | |
| 2023/0030637 A1 | 2/2023 | Gloeckner et al. | |
| 2023/0054937 A1 | 2/2023 | Chancy et al. | |
| 2023/0083906 A1 | 3/2023 | Jones et al. | |
| 2023/0310837 A1 | 10/2023 | Gamsizlar et al. | |

FOREIGN PATENT DOCUMENTS

| | | |
|---|---|---|
| EP | 2730299 A1 | 5/2014 |
| WO | 2009/026237 A1 | 2/2009 |
| WO | 2012016179 A1 | 2/2012 |
| WO | 2015019056 A1 | 2/2015 |
| WO | 2015105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |
| WO | 2021154427 A1 | 8/2021 |
| WO | 2022/159333 A1 | 7/2022 |
| WO | 2022/251425 A1 | 12/2022 |
| WO | 2023086394 A1 | 5/2023 |

OTHER PUBLICATIONS

PCT/US2022/012373 filed Jan. 13, 2022 International Search Report and Written Opinion dated Apr. 19, 2022.

PCT/US2022/049418 filed Nov. 9, 2022 International Search Report and Written Opinion dated Feb. 10, 2023.

U.S. Appl. No. 17/526,994, filed Nov. 15, 2021 Restriction Requirement dated Jan. 3, 2023.

U.S. Appl. No. 17/532,454, filed Nov. 22, 2021 Non-Final Office Action dated Mar. 22, 2023.

U.S. Appl. No. 17/561,504, filed Dec. 23, 2021 Non-Final Office Action dated Mar. 14, 2023.

U.S. Appl. No. 17/526,994, filed Nov. 15, 2021 Non-Final Office Action dated May 10, 2023.

U.S. Appl. No. 17/542,060, filed Dec. 3, 2021 Non-Final Office Action dated Jun. 27, 2023.

(56) References Cited

OTHER PUBLICATIONS

U.S. Appl. No. 17/561,458, filed Dec. 23, 2021 Non-Final Office Action dated Jun. 16, 2023.
U.S. Appl. No. 17/561,504, filed Dec. 23, 2021 Final Office Action dated Jul. 19, 2023.
U.S. Appl. No. 17/863,898, filed Jul. 13, 2022 Non-Final Office Action dated Jul. 17, 2023.
U.S. Appl. No. 17/902,705, filed Sep. 2, 2022 Non-Final Office Action dated May 24, 2023.
U.S. Appl. No. 17/373,568, filed Jul. 12, 2021 Non-Final Office Action dated Nov. 9, 2023.
U.S. Appl. No. 17/526,994, filed Nov. 15, 2021 Advisory Action dated Jan. 19, 2024.
U.S. Appl. No. 17/526,994, filed Nov. 15, 2021 Final Office Action dated Oct. 24, 2023.
U.S. Appl. No. 17/532,454, filed Nov. 22, 2021 Final Office Action dated Sep. 27, 2023.
U.S. Appl. No. 17/532,454, filed Nov. 22, 2021 Notice of Allowance dated Dec. 8, 2023.
U.S. Appl. No. 17/542,060, filed Dec. 3, 2021 Non-Final Office Action dated Nov. 28, 2023.
U.S. Appl. No. 17/561,458, filed Dec. 23, 2021 Final Office Action dated Sep. 12, 2023.
U.S. Appl. No. 17/561,458, filed Dec. 23, 2021 Notice of Allowance dated Dec. 6, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Nov. 22, 2023.
U.S. Appl. No. 17/902,705, filed Sep. 2, 2022 Advisory Action dated Oct. 19, 2023.
U.S. Appl. No. 17/902,705, filed Sep. 2, 2022 Final Office Action dated Aug. 17, 2023.
U.S. Appl. No. 17/902,705, filed Sep. 2, 2022 Non-Final Office Action dated Dec. 7, 2023.
U.S. Appl. No. 17/373,568, filed Jul. 12, 2021 Notice of Allowance dated Apr. 26, 2024.
U.S. Appl. No. 17/526,994, filed Nov. 15, 2021 Non-Final Office Action dated Apr. 22, 2024.
U.S. Appl. No. 17/542,060, filed Dec. 3, 2021 Notice of Allowance dated Jun. 3, 2024.
U.S. Appl. No. 17/796,604, filed Jul. 29, 2022 Notice of Allowance dated May 1, 2024.
U.S. Appl. No. 17/863,898, filed Jul. 13, 2022 Non-Final Office Action dated Mar. 11, 2024.
U.S. Appl. No. 17/902,705, filed Sep. 2, 2022 Final Office Action dated May 22, 2024.

* cited by examiner

DYNAMIC PRESSURE RESPONSE SYSTEM AND METHOD FOR MEASURING RESIDUAL FLUID

PRIORITY

This application claims the benefit of priority to U.S. Provisional Application No. 63/128,597, filed Dec. 21, 2020, which is incorporated by reference in its entirety into this application.

SUMMARY

Briefly summarized, embodiments disclosed herein are directed to a dynamic pressure response system configured for measuring residual fluid volume within a drainage tube of a fluid collection system. Current methods to measure fluid output, for example urine output in critical care patients, include collecting fluid in a drainage bag, container, or similar graduated or weight-based collection system. The flexibility of the drainage tube that communicates with the container can form sections of positive incline, where drainage fluid can accumulate, termed "dependent loops." A drawback of these systems is that fluid caught within the dependent loop can affect fluid output measurements. The clinician must manipulate the tubing to maneuver the residual fluid into the collection container to achieve an accurate measurement. However, in doing so, the clinician can risk inducing pressure spikes and/or potential fluid reflux into the patient. Further, the fluid caught in the tubing can dramatically affect fluid output measurements, resulting in an inaccurate patient diagnosis.

Embodiments disclosed herein are directed to dynamic pressure response systems configured to measure the volume of residual liquid caught within the tube lumen as dependent loops. The pressure response system measures the magnitude of pressure response after application of an air displacement bolus and determines a fluid volume. The pressure response system can be coupled with fluid measuring systems to provide a fully automated and highly accurate fluid drainage and measuring system.

Disclosed herein is a drainage system configured to drain a fluid from a body of a patient, the drainage system including, a drainage tube defining a drainage lumen and configured to provide fluid communication between a catheter and a collection container, a connector including a valve and configured to control fluid communication between the drainage lumen, a pump, and one of the catheter or the collection container, and a control logic configured to, i) provide an air displacement bolus to the drainage lumen, ii) displace a dependent loop from a neutral position to a displaced position, and iii) determine a volume of fluid within the drainage lumen.

In some embodiments, the control logic can modify one of the valve or the pump to provide the air displacement bolus to the drainage lumen. In some embodiments, the drainage system further includes a sensor disposed within the drainage lumen and communicatively coupled with the control logic, the sensor configured to detect a pressure of fluid within the drainage lumen. The connector is a distal connector disposed between the catheter and the drainage tube and configured to provide a positive air displacement bolus into the drainage lumen, distal to the dependent loop. The connector is a proximal connector disposed between the collection container and the drainage tube and configured to provide a negative air displacement bolus to the drainage lumen, proximal to the dependent loop. The control logic is communicatively coupled to an external computing device, handheld device, networked device, or electronic health record system. The catheter is a Foley catheter configured to drain a fluid from a bladder of a patient.

Also disclosed is a method of measuring a volume of fluid within a drainage lumen including, providing a positive air displacement bolus to a drainage lumen, distally of a dependent loop, displacing the dependent loop from a neutral position to a displaced position, measuring a change in air pressure in the drainage lumen, and determining a volume of fluid within the drainage lumen.

In some embodiments, the neutral position includes a distal meniscus and a proximal meniscus at substantially an equal vertical height. A displaced position includes a proximal meniscus being above the distal meniscus. In some embodiments, providing the positive air displacement bolus includes modifying one of a connector piece valve between a closed position and an open position, or an operation of a pump. The connector piece is disposed between a catheter and a collection container. The fluid is urine drained from a bladder of a patient.

Also disclosed is a method of measuring a volume of fluid within a drainage lumen including, providing a negative air displacement bolus to a drainage lumen, proximal of a dependent loop, displacing the dependent loop from a neutral position to a displaced position, measuring a change in air pressure in the drainage lumen, and determining a volume of fluid within the drainage lumen.

In some embodiments, the neutral position includes a distal meniscus and a proximal meniscus at substantially an equal vertical height. A displaced position includes a proximal meniscus being above the distal meniscus. In some embodiments, providing the negative air displacement bolus includes modifying one of a connector piece valve between a closed position and an open position, or an operation of a pump. The connector piece is disposed between a catheter and a collection container. The fluid is urine drained from a bladder of a patient.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
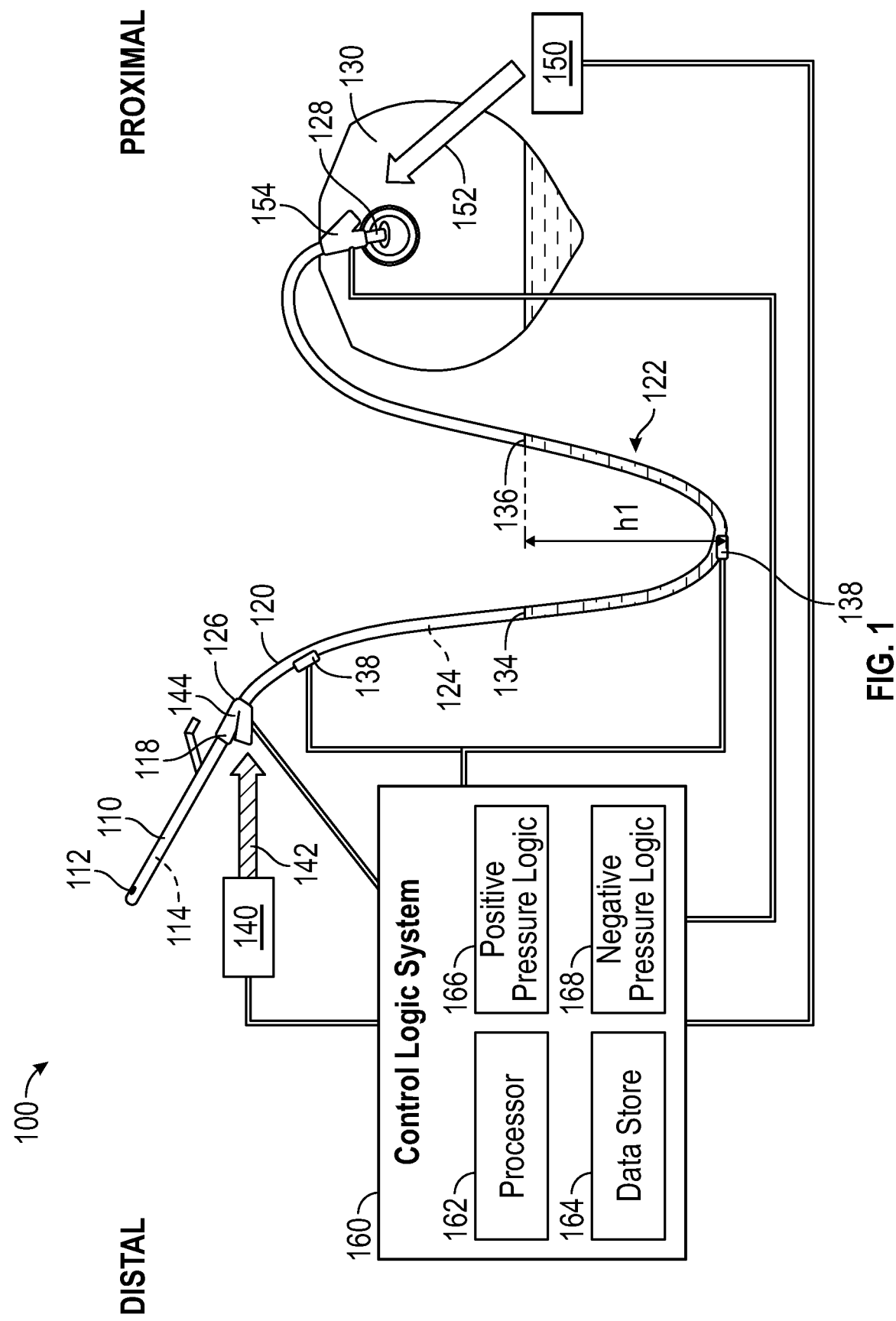
FIG. 1 shows an exemplary catheter and fluid collection system including a dynamic pressure response system before application of an air bolus, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, a longitudinal axis extends substantially parallel to an axial length of the drainage tube. A lateral axis extends normal to the longitudinal axis, and a transverse axis extends normal to both the longitudinal and lateral axes.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format. The term "computerized" generally represents that any corresponding operations are conducted by hardware in combination with software and/or firmware. As used herein, the term "fluid" can include a gas, liquid, or combination thereof. Unless defined otherwise, all technical and scientific terms used herein have the same meaning as commonly understood by those of ordinary skill in the art.

Embodiments disclosed herein are directed to a dynamic pressure response system including control logic configured to measure residual fluid disposed within a drainage tube lumen of a fluid collection system. The residual fluid volume is measured by detecting the magnitude of the dynamic pressure response in the system containing the residual fluid when a sudden displacement bolus of air volume (e.g.

increase or decrease) occurs inside the system. The pressure burst magnitude is related to the pressure needed to move the mass of fluid, thus the fluid volume can be calculated from measurements of the burst pressure. The magnitude of the measured air pressure exhibits a dynamic pressure response corresponding to the mass of fluid in the tube. Either positive or negative pressure bursts can be used to produce and measure the corresponding positive or negative dynamic response spike pressure.

FIG. 1 shows an exemplary pressure response drainage system ("system") 100, configured to drain a fluid from a patient. The system 100 generally includes a catheter 110, a drainage tube ("tube") 120, a collection container ("container") 130, and a control logic system 160. Exemplary catheters 110 include indwelling catheters, Foley catheters, balloon catheters, peritoneal drainage catheters, or the like, and are configured to be inserted into an orifice within the body of a patient to drain a fluid therefrom. Exemplary fluids can include water, blood, plasma, urine, interstitial fluid, saliva, mucus, pus, or the like. In an embodiment, the catheter 110 can be inserted through the urethra and into a bladder of a patient. However, it will be appreciated that embodiments disclosed herein can be used with various active or passive, bodily fluid drainage systems.

The catheter 110 includes an eyelet 112 that provides fluid communication with a lumen 114 of the catheter 110, and is configured to drain a fluid, e.g. urine, from a patient. The drainage tube 120 extends from a distal end 126 to a proximal end 128 to define an axial length, and defines a lumen 124. The distal end 126 of the tube 120 can be in fluid communication with a proximal 118 end of the catheter 110. The proximal end 128 can be in fluid communication with a collection container 130, to provide fluid communication between the lumen 114 of the catheter 110 and the collection container 130. The drainage tube 120 can be formed of rubber, plastic, polymer, silicone, or similar suitable material. The collection container 130 can include a rigid container, a flexible collection bag, or similar suitable container for receiving a fluid, e.g. urine, drained from the catheter 110.

As shown in FIG. 1, the flexibility of the drainage tube 120 can result in sections of the tube 120 providing a positive incline relative to the direction of fluid flow therethrough. These positive incline portions allow dependent loops 122 to form, which can lead to fluid pooling within the tube 120. The fluid caught within the dependent loop can result in inaccurate fluid output measurements and misdiagnoses of patients.

In an embodiment, a source of positive or negative air pressure, e.g. a pump or the like, can introduce an air displacement bolus (i.e. either positive or negative) into the tube lumen 124 to displace the residual fluid caught within the dependent loop 122 and determine an amount of fluid to be included in the fluid output measurements. In an embodiment, a pump 140 can introduce a positive air displacement bolus 142 at one of a distal connector piece 144, disposed adjacent the catheter 110, or a proximal connector piece 154, disposed adjacent the container 130. In an embodiment, a vacuum pump 150 can introduce a negative air displacement bolus 152 at one of a proximal connector piece 154, disposed adjacent the container 130, or a distal connector piece 144, disposed adjacent the catheter 110. Exemplary pumps can include peristaltic pumps, diaphragm pumps, solenoid pumps, compressors, medical air lines, medical vacuum lines, piston pumps, syringes, bellows, reciprocating pumps, combinations thereof, or the like.

Figure 3:
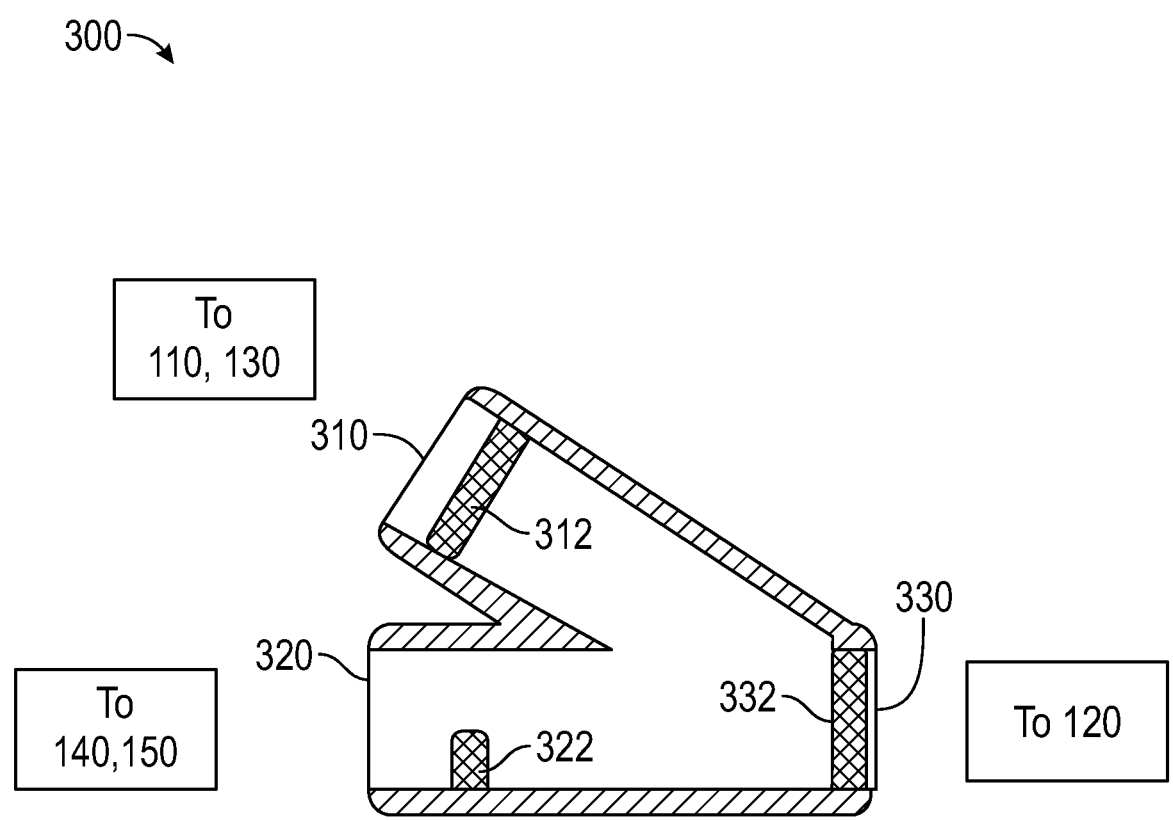
FIG. 3 shows a cross-section view of a connector piece, in accordance with embodiments disclosed herein.

In an embodiment, the system 100 can include a connector piece ("connector"), e.g. a distal connector piece 144 or a proximal connector piece 154. FIG. 3 shows further details of an exemplary connector piece 300. The connector piece 300 can include a first inlet 310 configured to couple with either an outlet of the catheter 110 or an inlet of the collection container 130 to provide fluid communication therebetween. The connector 300 can include a second inlet 320 configured to provide fluid communication with either the positive air pump 140 or vacuum pump 150. One or both of the first inlet 310 and the second inlet 320 can be in fluid commination with an outlet 330 of the connector piece 300 that is coupled with the drainage tube 120.

In an embodiment, the connector 300 can include one or more valves, e.g. solenoid valves, or the like, configured to control a fluid flow between one of the first inlet 310, second inlet 320, or outlet 330 of the connector 300. The first inlet 310 can include a first valve 312, a second inlet 320 can include a second valve 322, and the outlet 330 can include an outlet valve 332. The valve(s) 312, 322, 332, can be communicatively coupled with the control logic system 160 and can transition between a closed position, and one or more open positions. The one or more open positions can be between 1% open and 100% open. Advantageously, the one or more open positions can provide different flow rates or fluid pressures of a fluid therethrough. For example, the system 100 can modify the size of the positive air displacement bolus 142 or the negative air displacement bolus 152 applied to the tube lumen 124.

In an embodiment, the system 100 can close the first inlet valve 312 preventing fluid flow between the tube lumen 124 and one of the catheter lumen 114 or the container 130, prior to introducing the air displacement bolus 142, 152. This can prevent air flow from being diverted into or out of the catheter lumen 114 or the container 130 and can achieve an accurate pressure measurement, as described in more detail herein. Moreover, the patient can be isolated from the system 100 prior to application of the air displacement bolus 142, 152 mitigating pressure spikes, fluid reflux, or trauma to the patient.

In an embodiment, the connector 300 can include a second valve 322 disposed in the second inlet 320 and configured to control a volume of the air displacement bolus 142, 152 into or out of the tube lumen 124. In a closed position, the second valve 322 can prevent the introduction of an air displacement bolus 142, 152 to the tube lumen 124. The second valve 322 can open to one or more open positions (e.g. 1% to 100% of fully open) to control a volume of the air displacement bolus 142, 152. It will be appreciated that the connector piece 144 can include different numbers or configurations of inlets, outlets, and/or valves, which are contemplated to fall within the scope of the present invention.

In an embodiment, the positive air pressure pump 140 or vacuum pump 150 can operate at one or more speeds to provide one or more fluid flow rates or fluid pressures within the tube lumen 124. For example, the positive air pressure pump 140 or vacuum pump 150 can operate at a first speed to provide a first pressure, or at a second speed to provide a second pressure, different from the first pressure. In an embodiment, the pump 140 can shut down to provide no air pressure. In an embodiment, the system 100 can include a first pump providing a first pressure and a second pump providing a second pressure different from the first pressure. The connector 300 can include three of more inlets and configured to provide one of the first pressure from the first pump, or the second pressure from the second pump to the tube lumen 124. It will be appreciated that other numbers and configurations of connectors 300, pumps 140, 150, or the like, are also contemplated to fall within the scope of the present invention.

In an embodiment, the system 100 can further include a pressure response control logic ("control logic") 160. The control logic 160 can be communicatively coupled with one of the pump 140, the vacuum pump 150, the distal connector 144, the proximal connector 154, or one or more sensors 138. The control logic 160 can include a processor 162, a data store 164, and one or more logic modules, for example a positive pressure logic module 166, or a negative pressure logic module 168. In an embodiment, the control logic 160 can be communicatively coupled with one or more sensors 138 configured to detect one or more of an absolute pressure level, the presence of liquid, the relative humidity (RH) of the fluid, the presence of columnized fluid, or the presence of dependent loop(s) 122, within the tube lumen 124.

Figure 2:
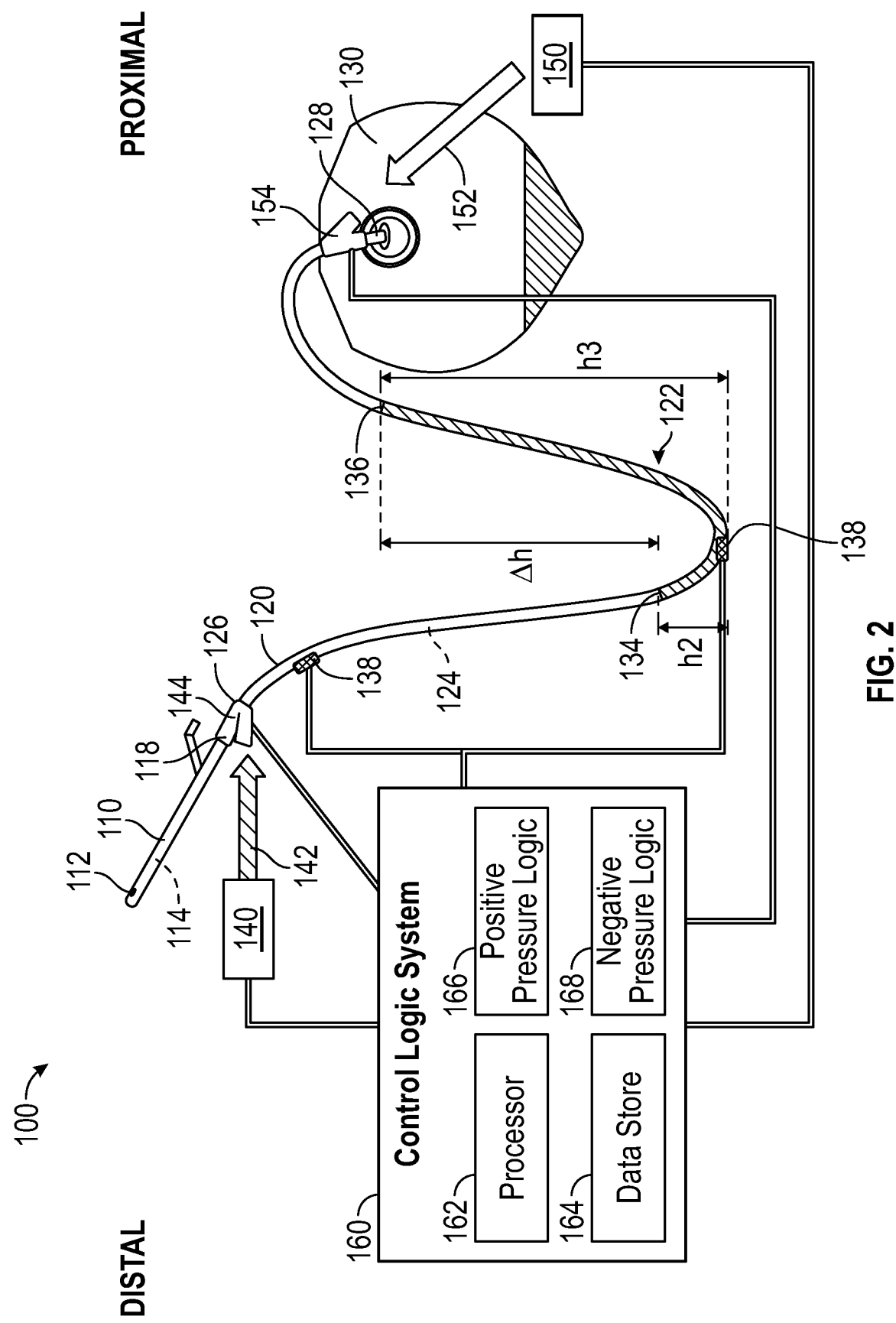
FIG. 2 shows an exemplary catheter and fluid collection system including a dynamic pressure response system after application of an air bolus, in accordance with embodiments disclosed herein.

In an embodiment, the control logic 160, for example the positive pressure logic 166, can send and receive signals to and from one of the pump(s) 140, 150, connectors 144, 154, or sensors 138 to provide a positive air displacement bolus 142 at the distal connector 144 that can displace a dependent loop 122 from a neutral position (e.g. FIG. 1), to a displaced position (e.g. FIG. 2). In an embodiment, the control logic 160, for example the negative pressure logic 168, can provide a negative air displacement bolus 152, for example at the proximal connector 154, which can displace a dependent loop 122 from a neutral position, (e.g. FIG. 1), to a displaced position, (e.g. FIG. 2).

As shown in FIG. 1, a dependent loop 122 in a neutral position includes a distal meniscus 134 disposed at the same vertical height (h1) as a proximal meniscus 136. In an embodiment, when a positive air displacement bolus 142, is introduced to the tube lumen 124 at the distal connector 144, the increase in air pressure distal of the dependent loop 122, i.e. distal of the distal meniscus 134, can transition the dependent loop 122 from the neutral position (FIG. 1) to the displaced position (FIG. 2), where a distal meniscus 134 is disposed at a lower vertical height (h2) and a proximal meniscus 136 is disposed at a higher vertical height (h3), above the height (h2) of the distal meniscus 134. In an embodiment, when a negative air displacement bolus 152, is introduced to the tube lumen 124 at the proximal connector 154, the decrease in air pressure proximal of the dependent loop 122, i.e. proximal of the proximal meniscus 136, can transition the dependent loop 122 from the neutral position (FIG. 1) to the displaced position (FIG. 2). To note, the displaced position does not transition any of the fluid from the tube lumen 124 to the container 130.

In an embodiment, the control logic 160 can include a sensor 138 configured to detect a difference in vertical height ($\Delta H$) between the distal meniscus 134 and the proximal meniscus 136. The control logic 160 can differentiate between a neutral position and a displaced position when the difference in vertical height ($\Delta H$) passes a threshold value. The threshold value can be predetermined or can be derived by the control logic 160. By way of non-limiting examples, exemplary sensors 138 configured to detect a difference in vertical height ($\Delta H$) can include ultrasonic sensors configured to determine a relative height of the meniscus 134, 136 based on a reflected sound wave, optical sensors configured to determine a relative height based on a reflected light wave, electrical impedance sensors disposed along a length of the tube 120, combinations thereof, or the like.

In an embodiment, the control logic 160 can measure a volume of the air displacement bolus required to displace the dependent loop 122 from the neutral position to the displaced position and can determine a volume of fluid within the dependent loop 122. In an embodiment, the control logic 160 can measure an air pressure (positive or negative) of the air displacement bolus required to displace the dependent loop 122 from the neutral position to the displaced position and can determine a volume of fluid within the dependent loop 122. In an embodiment, once the control logic 160 has determined a volume of fluid within the dependent loop 122, the control logic 160 can modify one or more valves within the connector 144, 154, 300 to release the air displacement bolus from the tube lumen 124 and allow the dependent loop 122 to resume the neutral position (FIG. 1).

In an embodiment, the control logic 160 provides an air displacement bolus to the tube lumen 124, for example, a positive air displacement bolus 142 introduced distal to the dependent loop 122 and can displace the dependent loop 122 to the displaced position (FIG. 2). As the dependent loop 122 returns to a neutral position, the volume of air within the tube 124 distal to the dependent loop 122 is compressed, increasing the air pressure. The control logic 160 can measure the increase in air pressure which is correlated with the volume of fluid within the tube lumen 124. For example, a larger volume of fluid will be relatively heavier and require a larger volume of air to displace the dependent loop 122, resulting in a larger air pressure once the dependent loop 122 resumes the neutral position. By measuring the volume of air displacement bolus and the change in air pressure within the tube lumen 124, the control logic 160 can determine a volume of fluid within the dependent loop 122.

In an embodiment, a negative air displacement bolus 152 can be introduced at a proximal connector 154. Worded differently, a volume of air within the tube lumen 124 can be removed by way of the proximal connector 154. As such, the negative air displacement bolus 152 can displace the dependent loop 122 from a neutral position (FIG. 1) to a displaced position (FIG. 2). As the fluid in the dependent loop 122 returns to a neutral position, the air pressure within the tube lumen 124 that is proximal of the dependent loop 122 can drop. The drop in air pressure can be proportional to the volume of fluid within the tube lumen 124. As such the control logic 160 can determine the volume of fluid within the tube lumen 124. Advantageously, embodiments including the negative pressure burst pressure response system 100 can include equipment (proximal connector 154, negative pressure pump 150, etc.) disposed adjacent the collection container 130 and away from the patient, providing a more compact system and mitigating impact to patient comfort.

In an embodiment, the positive air displacement bolus 142 can be introduced at the proximal connector 154 to displace the dependent loop 122 from the neutral position to a second displaced position. The second displaced position can include a distal meniscus 134 disposed at a higher height (h3) and a proximal meniscus disposed at a lower height (h2) such that the distal meniscus 134 is disposed above the proximal meniscus 136. Similarly, a negative air displacement bolus 152 can be introduced at the distal connector 144 to displace the dependent loop 122 from the neutral position to the second displaced position. The control logic 160 can determine a volume of fluid disposed within the dependent loop 122, as described herein.

The control logic 160 can be configured to provide the air displacement bolus 142, 152, in response to a trigger. The trigger can be a time-based trigger or an action-based trigger. For example, the control logic 160 can be triggered after a dynamic or predetermined time window has elapsed, or in response to an action such as an input from a user, an input from an automated system, or a signal from a sensor 138. In an embodiment, the sensor can detect the presence of a dependent loop 122 within the tube lumen 124, e.g. by a change in pressure, a change in impedance, or the like, as described herein. Advantageously, the pressure response system 100 can be fully automated to determine the presence of a dependent loop 122, close or open one or more valves 312, 322, 332, and determine a volume fluid within the tube lumen 124. As such, the pressure response system 100 and can be used in conjunction with other fluid output measurement systems (e.g. weight based, ultrasonic, impedance fluid measurement systems, etc. to determine a fluid volume within the container 130), to determine an accurate total fluid output from the patient. Further, the fully automated system 100 eliminates the need for a clinician to manipulate the tube 120 to maneuver residual liquid into the container 130 for accurate volume measurement. This reduces the potential risk of urine reflux into the patient bladder, reduces clinician workload and reduces the risk of human error.

In an embodiment, the pressure response system 100, i.e. the control logic 160, can store the fluid volume data to the data store 164. In an embodiment, the control logic 160 can be communicatively coupled, either wired or wirelessly, with one or more external computing systems. Exemplary external computing systems can include hand-held devices, laptop computers, consoles, servers, networked device, electronic health record (EHR) systems, or the like. Advantageously, these external computing devices can trigger the system 100 to operate or receive information about the volume of fluid disposed within the tube lumen 124.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system configured to drain a fluid from a body of a patient, the drainage system comprising:
   a drainage tube defining a drainage lumen and configured to provide fluid communication between a catheter and a collection container;
   a distal connector including a valve and configured to control fluid communication between the drainage lumen, a pump, and the catheter; and
   a control logic configured to:
   i) provide an air displacement bolus to the drainage lumen;
   ii) displace a dependent loop from a neutral position, where a distal meniscus and a proximal meniscus are at equal heights, to a displaced position, where the distal meniscus is at a different height within the drainage lumen, relative to the proximal meniscus; and
   iii) determine a volume of liquid within the drainage lumen by measuring an air pressure between the distal connector and the distal meniscus, while maintaining the dependent loop in the displaced position within the drainage lumen.

2. The drainage system according to claim 1, wherein the control logic can modify one of the valve or the pump to provide the air displacement bolus to the drainage lumen.

3. The drainage system according to claim 1, further including a sensor disposed within the drainage lumen and communicatively coupled with the control logic, the sensor configured to measure the air pressure within the drainage lumen.

4. The drainage system according to claim 1, wherein the distal connector is disposed between the catheter and the drainage tube and is configured to provide a positive air displacement bolus into the drainage lumen, distal to the dependent loop.

5. The drainage system according to claim 1, further including a proximal connector disposed between the collection container and the drainage tube and configured to provide a negative air displacement bolus to the drainage lumen, proximal to the dependent loop.

6. The drainage system according to claim 1, wherein the control logic is communicatively coupled to an external computing device, a handheld device, a networked device, or an electronic health record system.

7. The drainage system according to claim 1, wherein the catheter is a Foley catheter configured to drain the fluid from a bladder of the patient.

8. The drainage system according to claim 1, wherein subsequent to determining the volume of fluid within the drainage lumen, the control logic is further configured to modify the valve of the distal connector to release the air displacement bolus from the drainage lumen and allow the dependent loop to return from the displaced position back to the neutral position.

9. A method of measuring a volume of fluid within a drainage lumen, comprising:
   providing a positive air displacement bolus to the drainage lumen, distally of a dependent loop;
   displacing the dependent loop from a neutral position, where a distal meniscus and a proximal meniscus are at equal heights, to a displaced position, where the distal meniscus is at a different height relative to the proximal meniscus within the drainage lumen;
   measuring a change in air pressure in the drainage lumen between a connector piece and the distal meniscus; and
   determining the volume of liquid within the drainage lumen, while maintaining the dependent loop in the displaced position within the drainage lumen.

10. The method according to claim 9, further including closing a first valve of the connector piece, which controls fluid communication between a catheter and the drainage lumen, prior to providing the positive air displacement bolus.

11. The method according to claim 9, wherein the displaced position includes the proximal meniscus being above the distal meniscus.

12. The method according to claim 9, wherein providing the positive air displacement bolus includes modifying one of a second valve of the connector piece between a closed position and an open position, or an operation of a pump.

13. The method according to claim 9, wherein the connector piece is disposed between a proximal end of a catheter and a distal end of the drainage lumen.

14. The method according to claim 9, wherein the liquid is urine drained from a bladder of a patient.

15. The method according to claim 9, further including subsequent to determining the volume of fluid within the drainage lumen, releasing the positive air displacement bolus from the drainage lumen and allowing the dependent loop to return from the displaced position back to the neutral position.

16. A method of measuring a volume of fluid within a drainage lumen, comprising:
- providing a negative air displacement bolus to the drainage lumen, proximal of a dependent loop;
- displacing the dependent loop from a neutral position, where a distal meniscus and a proximal meniscus are at equal heights, to a displaced position, where the distal meniscus is at a different height within the drainage lumen relative to the proximal meniscus;
- measuring a change in air pressure in the drainage lumen; and
- determining the volume of liquid within the drainage lumen from the change in air pressure, while maintaining the dependent loop in the displaced position within the drainage lumen.

17. The method according to claim 16, further including modifying a valve of a distal connector piece from an open position and a closed position prior to providing the negative air displacement bolus, the distal connector piece disposed between a proximal end of a catheter and a distal end of the drainage lumen.

18. The method according to claim 16, wherein the displaced position includes the proximal meniscus being above the distal meniscus.

19. The method according to claim 16, wherein providing the negative air displacement bolus includes modifying one of a valve of a proximal connector piece between a closed position and an open position, or modifying an operation of a pump.

20. The method according to claim 19, wherein the proximal connector piece is disposed between a proximal end of the drainage lumen and a collection container.

21. The method according to claim 16, wherein the liquid is urine drained from a bladder of a patient.

22. The method according to claim 16, further including subsequent to determining the volume of fluid within the drainage lumen, releasing the negative air displacement bolus from the drainage lumen and allowing the dependent loop to return from the displaced position back to the neutral position.

* * * * *